(12) United States Patent
Muske et al.

(10) Patent No.: US 12,102,162 B2
(45) Date of Patent: Oct. 1, 2024

(54) METHOD AND APPARATUS FOR HEAD PROTECTION AND PROVIDING AIR FLOW

(71) Applicant: Illinois Tool Works Inc., Glenview, IL (US)

(72) Inventors: Mitchell James Muske, Neenah, WI (US); Joseph C. Schneider, Greenville, WI (US); Moon Young Huh, Seoul (KR)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 17/701,217

(22) Filed: Mar. 22, 2022

(65) Prior Publication Data

US 2022/0211136 A1    Jul. 7, 2022

Related U.S. Application Data

(62) Division of application No. 16/556,870, filed on Aug. 30, 2019, now Pat. No. 11,278,077.

(60) Provisional application No. 62/726,148, filed on Aug. 31, 2018.

(51) Int. Cl.
    *A42B 3/20*        (2006.01)
    *A42B 3/04*        (2006.01)
    *A42B 3/28*        (2006.01)

(52) U.S. Cl.
    CPC ............... *A42B 3/20* (2013.01); *A42B 3/044* (2013.01); *A42B 3/288* (2013.01)

(58) Field of Classification Search
    CPC ........... A42B 3/22; A42B 3/222; A42B 3/225; A42B 3/226
    See application file for complete search history.

(56) References Cited

U.S. PATENT DOCUMENTS

| | | | |
|---|---|---|---|
| 5,467,480 A * | 11/1995 | Baudou | A42B 3/222 2/424 |
| 6,282,726 B1 | 9/2001 | Noyerie | |
| 7,594,278 B2 | 9/2009 | Huh | |
| 7,934,846 B1 * | 5/2011 | Schwanz | A61F 9/06 362/106 |
| 9,033,535 B2 * | 5/2015 | Robinson | F21K 9/65 362/276 |
| 2010/0223707 A1 | 9/2010 | Moyses | |
| 2011/0023204 A1 | 2/2011 | Brace | |

(Continued)

FOREIGN PATENT DOCUMENTS

| | | |
|---|---|---|
| CA | 02503167 | 10/2006 |
| WO | 2016044071 | 3/2016 |

OTHER PUBLICATIONS

Int'l Search Report and Written Opinion Appln. No. PCT/US2019/049141 mailed Dec. 16, 2019 (13 pgs).

*Primary Examiner* — Katherine M Moran

(74) *Attorney, Agent, or Firm* — McAndrews, Held & Malloy, Ltd.

(57) ABSTRACT

Example hard hat adapters include: a coupling mechanism to removably couple the hard hat adapter to a hard hat; an upper arm configured to removably couple to an outer face shield and an inner face shield; and a lower arm configured to removably couple to a blower shell, wherein the outer face shield and the inner face shield are configured to removably couple to the hard hat adapter at a first pivot point of the hard hat adapter.

9 Claims, 10 Drawing Sheets

(56) References Cited

U.S. PATENT DOCUMENTS

| | | |
|---|---|---|
| 2014/0034049 A1* | 2/2014 | Castiglione .............. A62B 7/10 |
| | | 128/202.27 |
| 2015/0359680 A1 | 12/2015 | Gardner |
| 2017/0112226 A1 | 4/2017 | Watkins |
| 2019/0175411 A1* | 6/2019 | Awiszus ................. A41D 13/12 |
| 2020/0297060 A1 | 9/2020 | Berggren |
| 2020/0405000 A1 | 12/2020 | Nilsson |
| 2021/0161716 A1 | 6/2021 | Watkins |

* cited by examiner

METHOD AND APPARATUS FOR HEAD PROTECTION AND PROVIDING AIR FLOW

CLAIM OF PRIORITY

This patent application is a divisional application of U.S. patent application Ser. No. 16/556,870 (now U.S. Pat. No. 11,278,077), filed Aug. 30, 2019, and claims priority to and claims benefit from United States Provisional Patent Application Ser. No. 62/726,148, filed on Aug. 31, 2018. The above identified application is hereby incorporated herein by reference in its entirety.

BACKGROUND

The present disclosure relates to providing protection to a head of a user, and more particularly, to a method and apparatus for head protection and providing air flow.

Limitations and disadvantages of conventional systems for providing head protections and air to an interior of a protection device worn by a user, such as, for example, powered air purifying respirators, will become apparent to one of skill in the art, through comparison of such approaches with some aspects of the present method and system set forth in the remainder of this disclosure with reference to the drawings.

SUMMARY

Methods and systems are provided for a method and apparatus for head protection and providing air flow, substantially as illustrated by and described in connection with at least one of the figures, as set forth more completely in the claims.

BRIEF DESCRIPTION OF THE DRAWINGS

These and/or other aspects will become apparent and more readily appreciated from the following description of some example embodiments, taken in conjunction with the accompanying drawings.

The drawings are not necessarily to scale. Where appropriate, similar or identical reference numbers are used to identify similar or identical elements.

DETAILED DESCRIPTION

Head protection devices used for various purposes may also provide air flow during use. The air flow may be used to, for example, cool the user during welding, grinding, etc. While there may be head protection devices such as, for example, helmets that may be used for a specific activity such as welding, it may be useful to have a head protection device that can be used for multiple purposes such as welding, grinding, cutting, etc. However, if the user is wearing a multi-purpose protection device, then it would be beneficial to allow the protection device to have weight and balance that is comfortable for the user, as well as allowing the user to access their face without removing the protection device.

A head protection device that provides air flow may be referred to as a PAPR (powered air-purifying respirator) helmet. With conventional PAPR welding helmets, the user would need to take the helmet off in order to, for example, communicate, eat, drink, etc. Disclosed PAPR helmets allow the user (wearer) easy access to their face without having to remove the entire helmet. The PAPR helmet may be, for example, a hard hat PAPR helmet in which the PAPR components are attached or affixed to a conventional hard hat.

Figure 1:
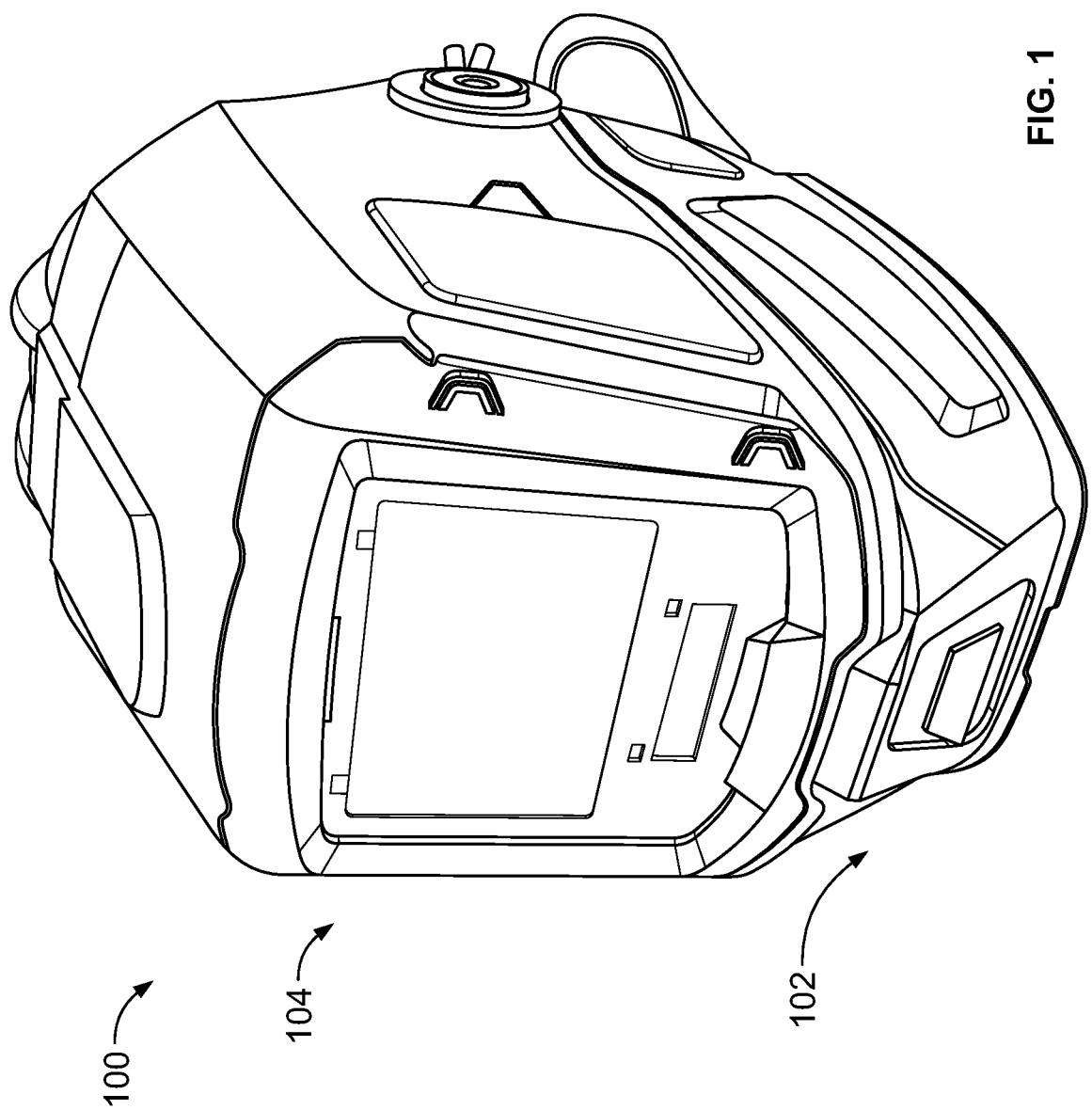
FIG. 1 is a drawing of an example head protection device in accordance with aspects of the disclosure.

FIG. 1 is a drawing of an example head protection device 100. Referring to FIG. 1, there is shown a head protection device 100 that comprises a blower shell 102 and shield 104. The shield 104 may comprise a single shield or multiple shields for different use cases. The example shield 104 is rotatable so that the user can raise the shield 104 away from the face without removing the head protection device 100.

Therefore, by rotating the shield 104, some example head protection devices allow the user to have access to his face while keeping the blower shell 102 of the head protection device 100 stationary. This is shown in more detail in FIG. 3. The blower shell 102 may comprise a blower vent 402 and a head seal 404 (FIG. 4). Accordingly, the operator may have access to their face by lifting the shield 104 while keeping the head seal 404 in place.

Additionally, while the example head protection device 100 shows the shield 104 vertically above the blower shell 102, other examples of the disclosure may have at least a portion of the shield 104 overlap the blower shell 102, or have at least a portion of the shield 104 below the blower shell 102 when the shield 104 is in a down position.

Figure 2:
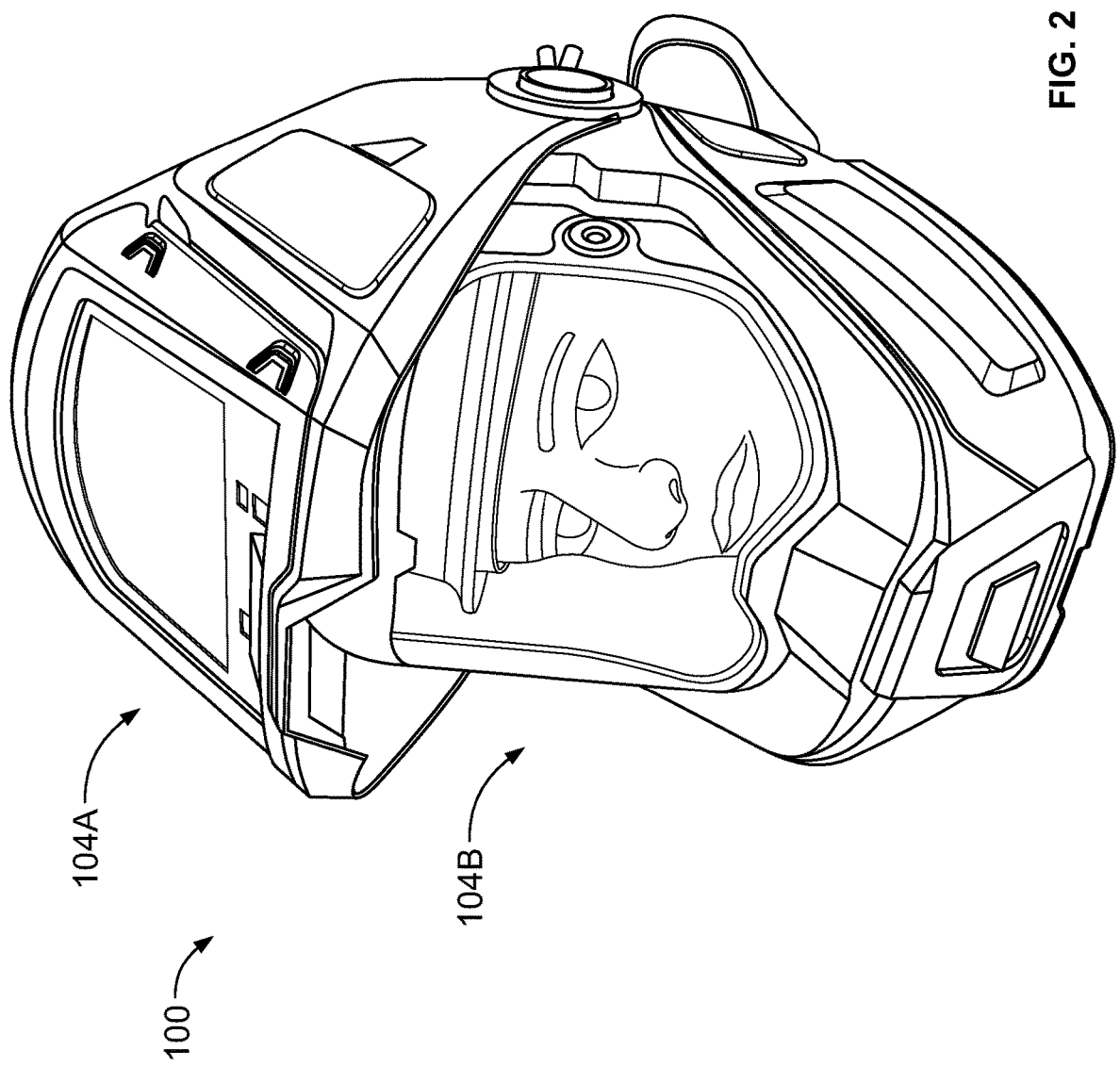
FIG. 2 is a drawing of an example head protection device with multiple shields where the outer face shield is raised in accordance with aspects of the disclosure.

In the example of FIG. 2, the shield 104 the shield includes an outer face shield 104A and an inner face shield 104B. Accordingly, as described above, at least a portion of one or both of the outer face shield 104A and inner face shield 104B may be vertically below the blower shell 102. The outer face shield 104A may be, for example, a welding shield, and the inner face shield 104B may be, for example, a grinding shield, a cutting shield, etc. The outer face shield 104A includes a darkening lens or auto-darkening filter (ADF) to protect the user's vision from the brightness of the welding arc. The inner face shield 104B includes a lens or other shield that has little or no darkening to enable the user to see in lower-light environments.

Figure 3:
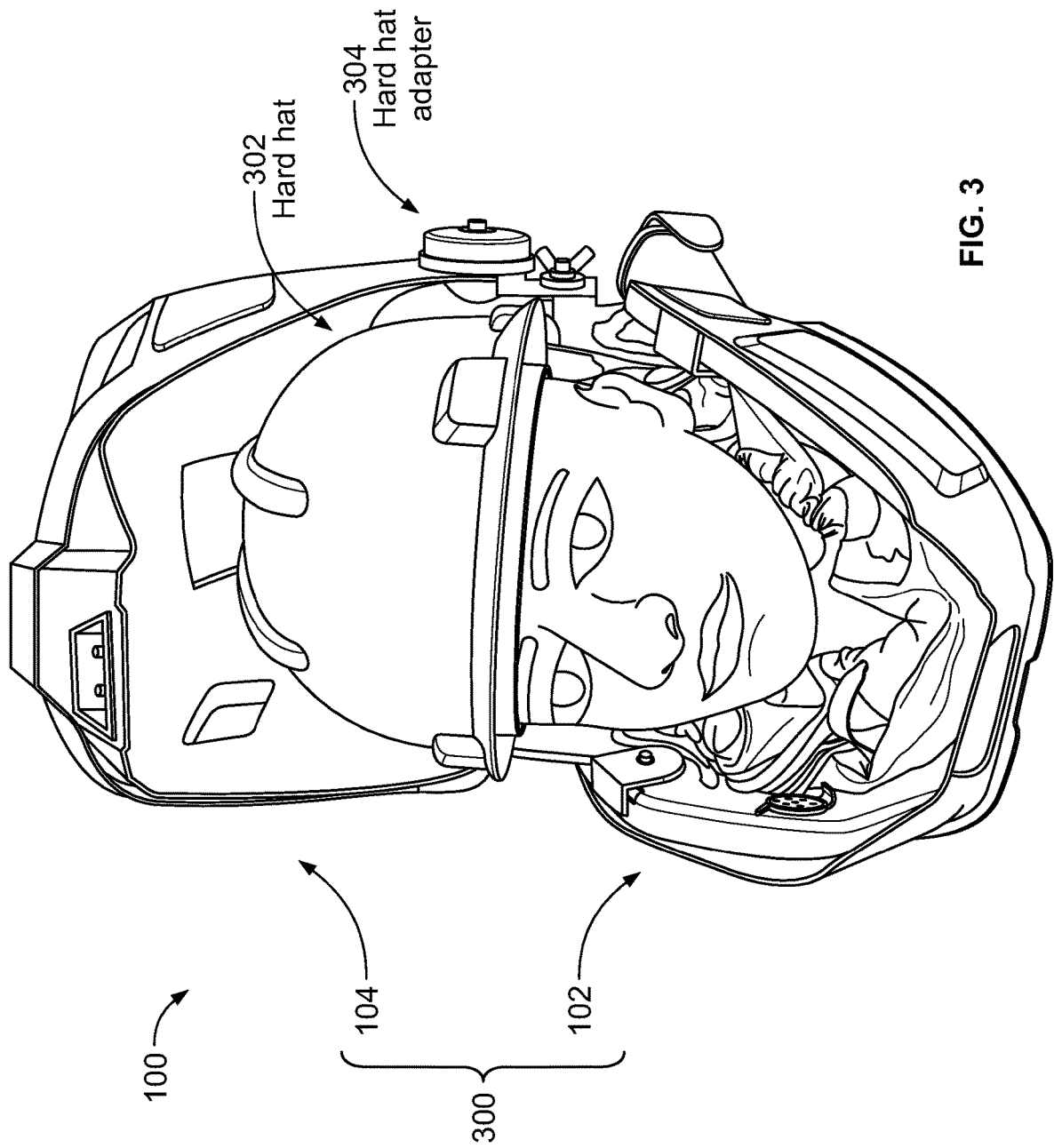
FIG. 3 is a drawing of an example head protection device with multiple shields where both the outer face shield and the inner face shield are raised in accordance with aspects of the disclosure.
Figure 4:
FIG. 4 is a close-up view of an example interior near a lower chin portion in an example head protection device in accordance with aspects of the disclosure.

The head protection device 100 may be used in three different modes of operation: weld mode (FIG. 1), grind mode (FIG. 2), and open face mode (FIG. 3). Accordingly, the weld mode may be a first mode where the outer face shield 104A is lowered and the inner face shield 104B is lowered. The grind mode may be a second mode where the outer face shield 104A is raised and the inner face shield 104B is lowered. The open face mode may be a third mode in which the outer face shield 104A is raised and the inner face shield 104B is raised so that the user will have access to the user's face, and will be able to view a workpiece that is being worked on.

Figure 9:
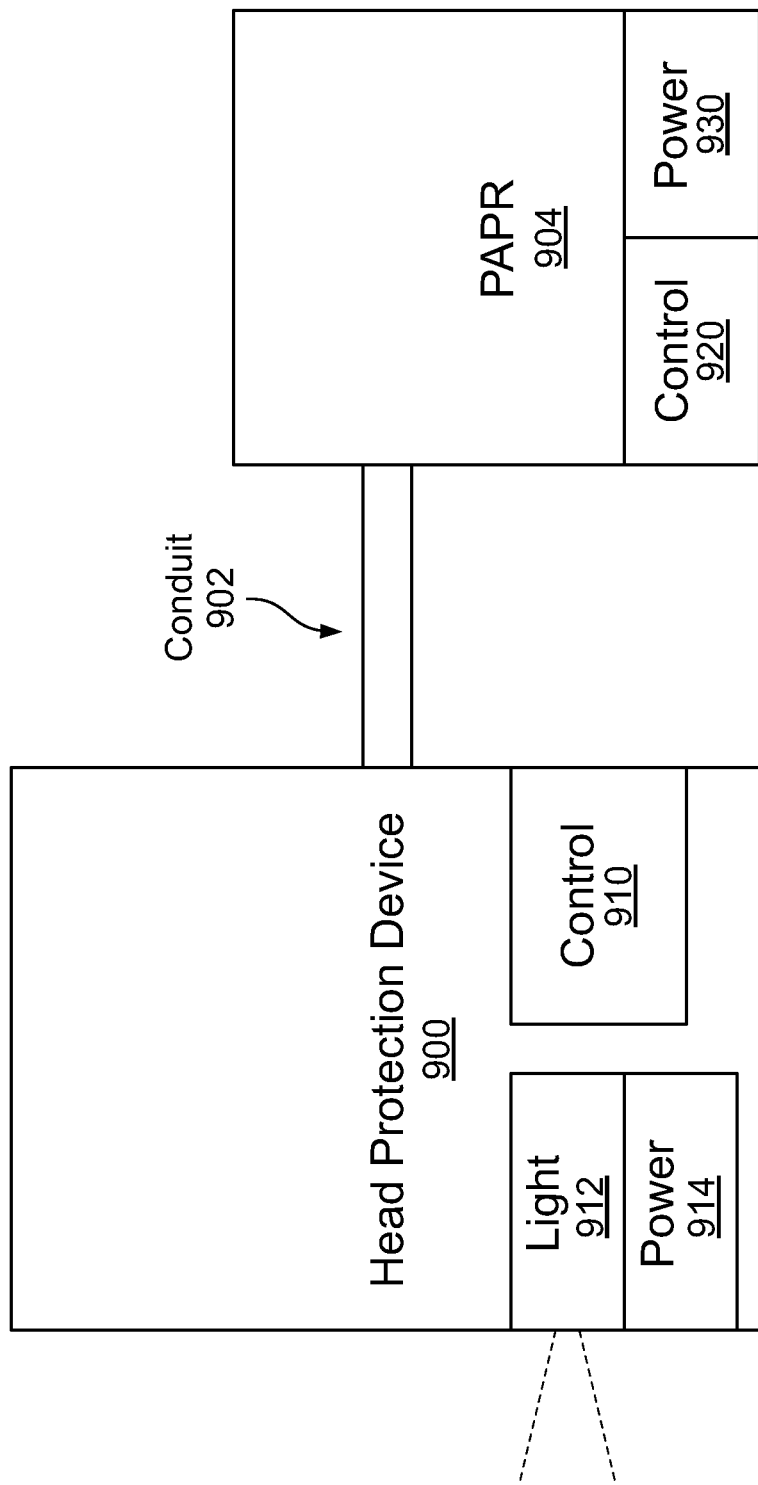
FIG. 9 is a drawing of an example configuration of a head protection device in accordance with aspects of the disclosure.

The blower vent 402 may be connected to an air manifold 508 (FIG. 5) that may provide air from an external device (PAPR 904 in FIG. 9). The air flow provided by the PAPR 904 is described in more detail with regard to FIG. 9.

FIG. 2 is a drawing of an example head protection device 100 with multiple shields where the outer face shield is raised. Referring to FIG. 2, there is shown the head protection device 100 that comprises multiple shields 104A and 104B. The outer face shield 104A may be, for example, a welding shield and the inner face shield 104B may be, for example, a grinding shield 104B. When the additional protection of the outer face shield 104A is not needed for non-welding purposes, the outer face shield 104A may be rotated out of the way to allow better vision for grinding, cutting, drilling, sanding, etc.

FIG. 3 is a drawing of an example head protection device 100 with multiple shields where both the outer face shield and the inner face shield are raised. Referring to FIG. 3, there is shown the head protection device 100 where the shield 104, which may comprise multiple shields 104A and 104B, is raised to expose the face. The outer face shield 104A may be, for example, a welding shield and the inner face shield 104B may be, for example, a grinding shield. When protection is not needed for the user, for example, when the user is taking a break for a snack or a drink, inspecting a work piece, etc., the outer face shield 104A and the inner face shield 104B may be rotated out of the way.

Accordingly, with the shield 104 raised, it can be seen that the head protection device 100 also comprises a hard hat 302 and a hard hat adapter 304 that allows a protection shell 300 to be mounted to the hard hat 302. The protection shell 300 may comprise, for example, the blower shell 102 and the shield 104. The blower shell 102 can be used for PAPR functionality where air can be provided for the user. As the blower shell 102 does not move when either of the outer face shield 104A or the inner face shield 104B is moved, air is provided to the user at a substantially constant location. In some embodiments, different air speeds may be provided when the shield 104A or 104B is raised or lowered. This will be discussed in more detail with respect to FIG. 9.

Some examples of the head protection device 100 may be a constructed unit that is manufactured with the protection shell 300, the hard hat 302, and the hard hat adapter 304. In other examples, a protection shell 300 may be fitted on to a hard hat 302 with an appropriate hard hat adapter 304 by, for example, selecting the appropriate parts. Accordingly, various embodiments of the disclosure may provide the head protection device 100 as a unit or pieces that are assembled as the head protection device 100 from individual parts (blower shell 102, shield 104, hard hat 302, and hard hat adapter 304, where one or more of these parts may have accessories associated with them) to allow for customization according to a user's preference.

FIG. 4 is a close-up view of an example interior near a lower chin portion in an example head protection device 100. Referring to FIG. 4, there is shown the head protection device 100 with an example placement of the blower vents 402 and the head seal 404. As can be seen, the blower vents 402 and the head seal 404 are not affected by whether the shield 104 is raised or lowered. Accordingly, the head seal 404 may remain in place while the shield 104 is moved. Furthermore, although two blower vents 402 are shown, other example head protection devices may have a different number of blower vents 402, whether one blower vent 402 or three or more blower vents 402.

Figure 5:
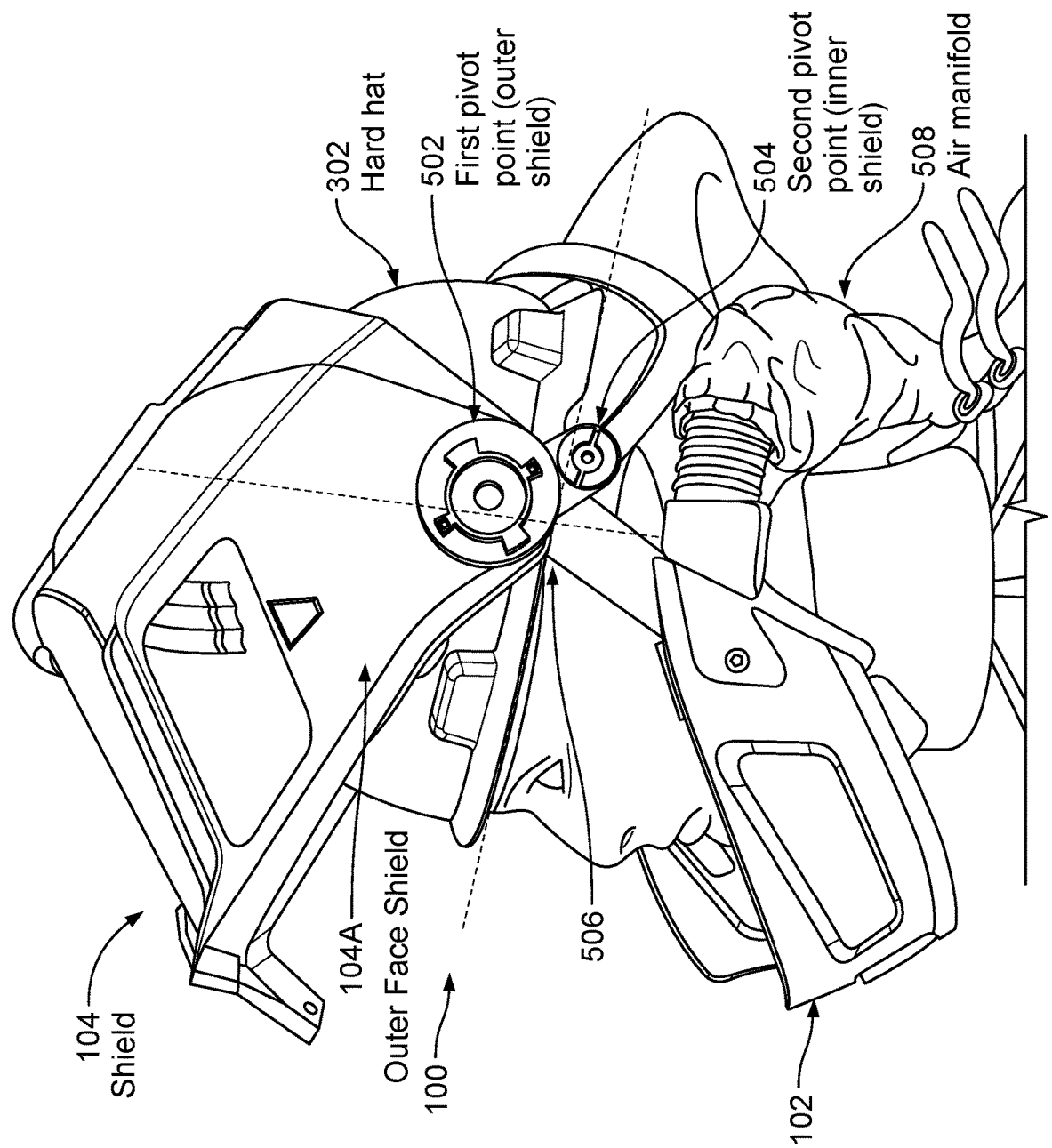
FIG. 5 is a view of example pivot points of an example head protection device in accordance with aspects of the disclosure.

FIG. 5 is a view of example pivot points of an example head protection device 100. Referring to FIG. 5, there is shown the head protection device 100 with first and second pivot points 502 and 504 for the outer and inner face shields 104A and 104B, respectively. An embodiment of the disclosure may have the first pivot point 502 for the outer face shield 104A that is different than the second pivot point 504 for the inner face shield 104B. The pivot points 502, 504 provide improved balance and placement of the center of gravity for the head protection device 100 whether the shield 104 is raised or lowered. For example, the placement of the second pivot point 504 may be to optimize the clearance of the inner face shield 104B over the hard hat 302 when the inner face shield 104B is raised to keep the center of gravity low for the head protection device 100. The optimization may be due to, for example, reducing the clearance of the inner face shield 104B over the hard hat 302 when the inner face shield 104B is raised.

Furthermore, with respect to the center point 506 of the hard hat 302, the second pivot point 504 can be seen to be below and behind the center point 506, which is also below and behind the first pivot point. Since the center point 506 is at the bottom of the hard hat 302, and at the center of the hard hat 302 in the front to back direction, the second pivot point 504 for the inner face shield located below and behind the center point 506 allows a low center of gravity when the outer face shield 104A and inner face shield 104B are raised.

There is also an air manifold 508 connected to the blower vents 402. The air manifold 508 may be used to deliver air from, for example, a PAPR 904 shown in FIG. 9.

As can be seen in FIG. 5, the term "below" refers to a downward, vertical direction and the term "behind" refers to a rear-ward, horizontal direction with respect to the head protection device (away from the shields 104).

Figure 6:
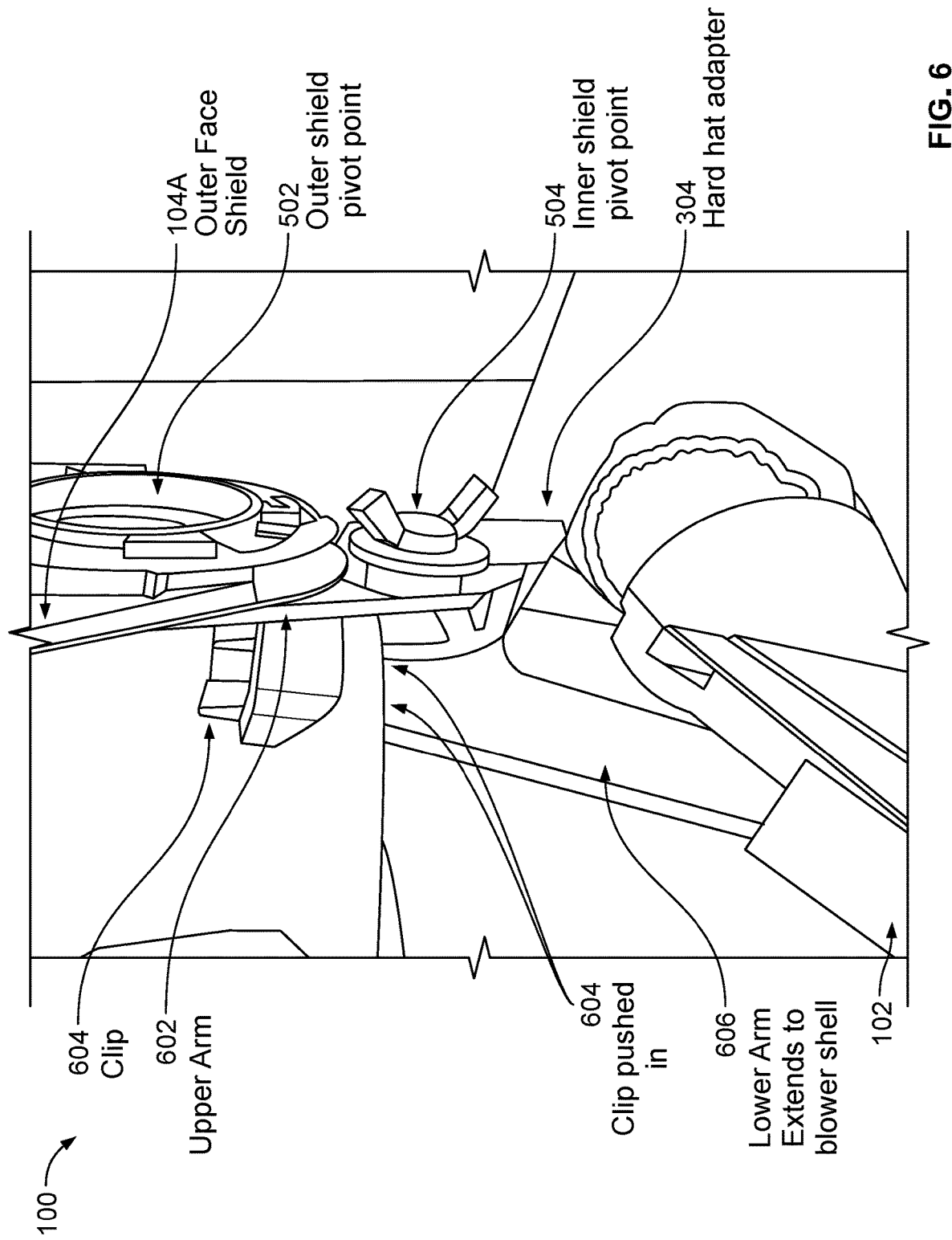
FIG. 6 is a close-up view of an example hard hat adapter used with an example head protection device in accordance with aspects of the disclosure.

FIG. 6 is a close-up view of an example hard hat adapter 304 used with an example head protection device 100. Referring to FIG. 6, there is shown the hard hat adapter 304 comprising an upper arm 602, a clip 604, and a lower arm 606. The upper arm 602 may be used to removably couple the outer face shield 104A and the inner face shield 104B to the hard hat adapter 304. The clip 604 may be used to removably couple the hard hat adapter 304 to the hard hat 302. The lower arm 606 may be used to removably couple the blower shell 102 to the hard hat adapter 304.

The outer face shield 104A may rotate about the first pivot point 502, and the inner face shield 104B may rotate about the second pivot point 504. When the inner face shield 104B rotates, the upper arm 602 rotates with the inner face shield 104B about the second pivot point 504. When both the outer face shield 104A and the inner face shield 104B are rotated together about the second pivot point 504, then the upper arm 602 also rotates about the second pivot point 504.

When the outer face shield 104A and the inner face shield 104B are lowered, the outer face shield 104A may be raised without raising the inner face shield 104B. The outer face shield 104A and the inner face shield 104B may also be raised together. When the outer face shield 104A and the inner face shield 104B are raised, the inner face shield 104B may be lowered without lowering the outer face shield 104A. The outer face shield 104A and the inner face shield 104B may also be lowered together.

While FIG. 6 shows the head protection device 100 comprising several pieces removably coupled together, various embodiments of the disclosure may have the head protection device 100 manufactured such that some parts may not be removable or replaceable. Accordingly, customization of a head protection device 100 may range from being able to select each individual part to couple to the hard hat adapter 304 to form the head protection device 100 to selecting the head protection device 100 as a single unit.

Figure 7:
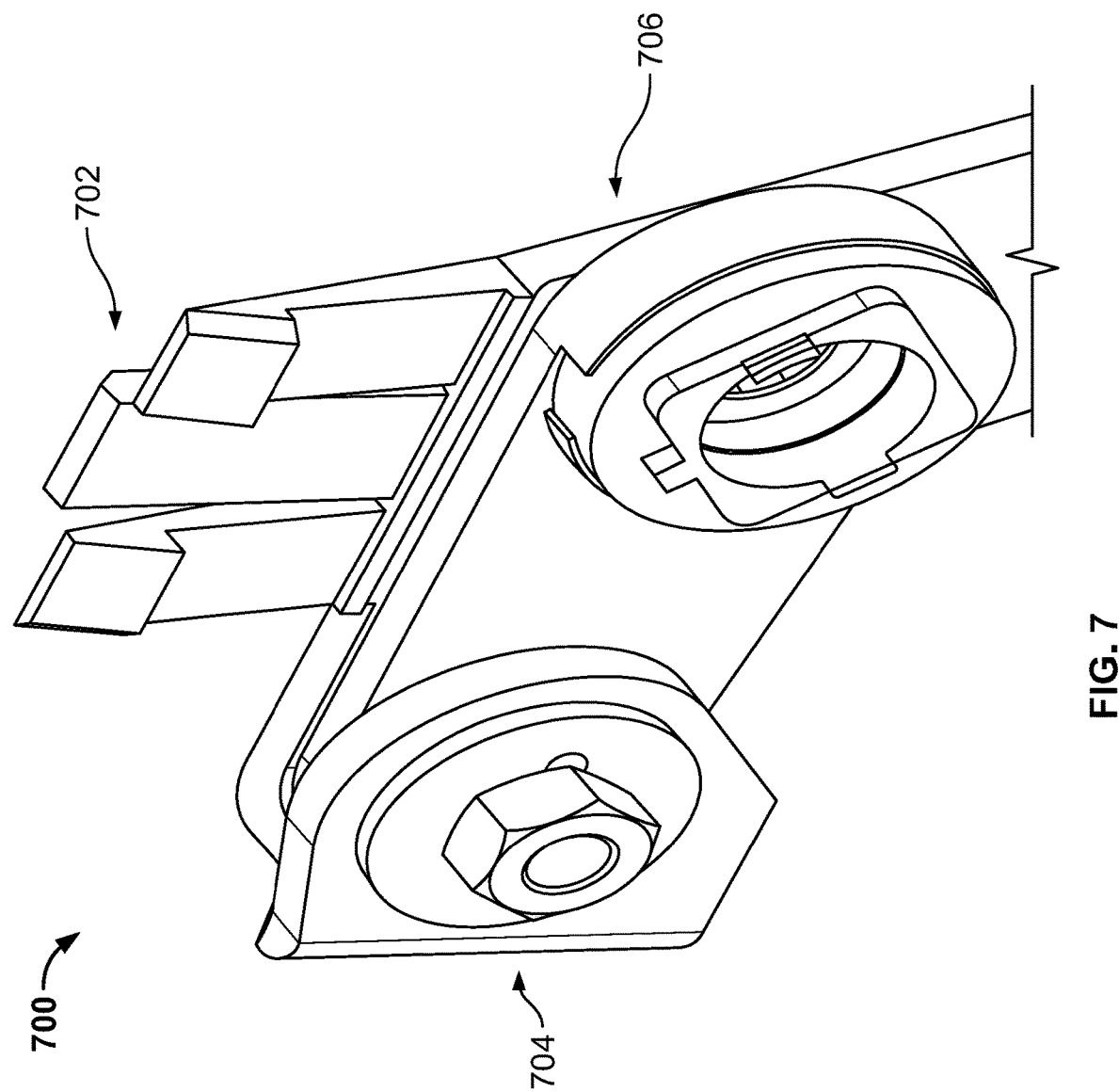
FIG. 7 is a drawing of an example hard hat adapter in accordance with a aspects of the disclosure.

FIG. 7 is a drawing of an example hard hat adapter in accordance with an embodiment of the disclosure. Referring to FIG. 7, there is shown the hard hat adapter 700 that is similar to the hard hat adapter 304. The hard hat adapter comprises a clip 702, an upper arm 704, and a lower arm 706 as described previously.

Figure 8:
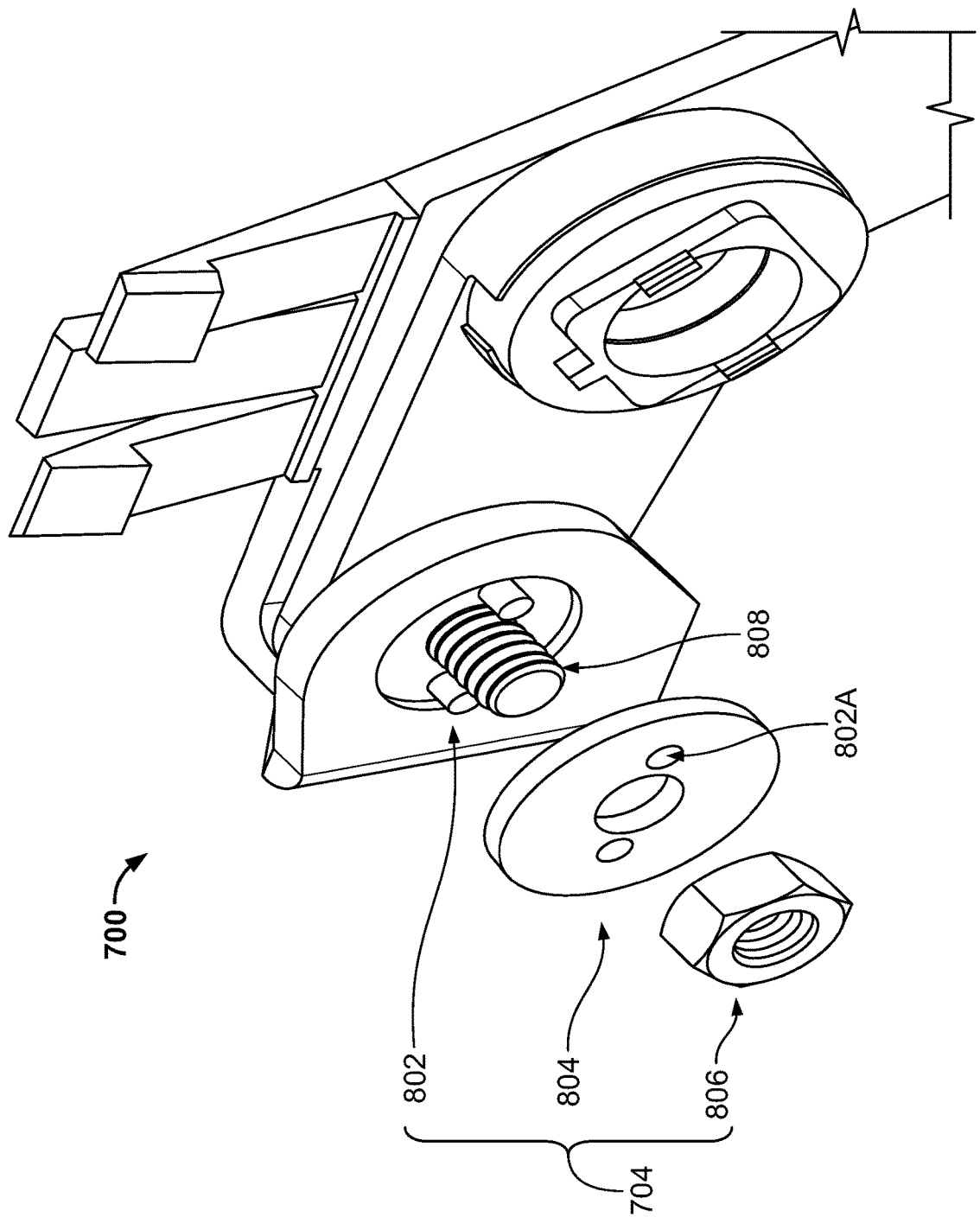
FIG. 8 is a partially exploded view of an example hard hat adapter in accordance with aspects of the disclosure.

FIG. 8 is a partially exploded view of an example hard hat adapter 100. Referring to FIG. 8, there is shown an embodiment of the hard hat adapter 700 where the upper arm 704 comprises an arm washer 804, a nut 806, and a bolt 808. In this embodiment, the arm washer 804 may be mechanically secured to the upper arm 704 via the securing pins 802 being inserted into corresponding holes 802A in the arm washer 804. This may prevent the nut 806 from backing off as a result of repeated raising and lowing of the inner face shield 104B. Various embodiments may not have the securing pins 802, or may use other methods to keep the nut 806 from backing off. For example, there may be dual nuts 806, there may be a retaining pin (not shown) inserted in a hole (not shown) in the bolt 808, etc. The retaining pin may be, for example, a cotter pin, a hair pin clip, etc.

FIG. 9 is a drawing of an example configuration of a head protection device in accordance with an embodiment of the disclosure. Referring to FIG. 9, there is shown a head protection device 900, a conduit 902, and a powered air-purifying respirator (PAPR) 904. The head protection device 900 may have coupled to it control circuitry 910 and a light source 912. There may also be a power source 914, which may be, for example, a battery, or power circuitry that receives power from outside the head protection device 900. The power may be received via electrical conductors or wirelessly. The power may be used for the control circuitry 910 as well as for the light 912. The control circuitry 910 and the light source 912 may be located in any suitable place on the head protection device 900. For example, the control circuitry 910 may be located on one side of the blower shell 102, and the light source 912 may be located on the other side of the blower shell 102. As another example, the light source 912 and the control circuitry 910 may be on the same side of the blower shell 102.

In various embodiments, the light source 912 may be removably coupled to the head protection device 100. For example, the light source 912 may be clipped on to the blower shell 102, fastened using a hook-and-loop fastener, placed in a holder, etc. Other embodiments may have the light source 912 built into, for example, the blower shell 102.

The light source 912 may be configured to, for example, turn on when the outer face shield 104A is raised and turn off when the outer face shield 104A is lowered. The light source 912 may also be configured to, for example, emit different colored light based on whether the outer face shield 104A is raised or lowered, whether the inner face shield 104B is raised or lowered, etc. The light source 912 may comprise one or more light sources that can be pointed to a specific area in front of the head protection device 900.

The control circuitry 910 may be used to control turning on and off the light source 912, and/or changing the color of the light emitted by the light source 912. The control circuitry 910 may also be used to set-up the automatic turning on/off the light of the light source 912, as well as determining when the light emitted by the light source 912 changes colors.

The raising and lowering of the outer face shield 104A and/or the inner face shield 104B may be determined by a sensor such as, for example, a switch. Other types of sensors may also be used from any of the various types of sensors available for detecting movement. For example, raising or lowering a shield may interrupt a light beam that is detected by a light sensor. The control circuitry 910 may comprise input and output devices, as well as a processor and memory. The control circuitry 910 is described in more detail in FIG. 10.

In an embodiment, information regarding detection of the raising and lowering of the shields 104A/104B may also be sent to the PAPR 904 via electrical conductors that may be, for example, part of the conduit 902, or wirelessly from the head protection device 900 to the PAPR 904. The PAPR 904 may then adjust the blower speed appropriately to either lower or raise the air flow speed. For example, when both shields 104A and 104B are lowered, the PAPR 904 may provide a first air flow, and when the outer face shield 104A is raised but the inner face shield 104B is lowered, the PAPR 904 may provide a second air flow that has a smaller air flow speed than an air flow speed of the first air flow. When both shields 104A and 104B are raised, the PAPR 904 may, for example, turn off the air flow to the head protection device 100.

In addition to the automatic signaling by the head protection device 900, a user may also be able to directly control the PAPR via a user interface such as with the input devices 1042 of the control circuitry 910. The input device 1042 may comprise, for example, buttons, switches, rotary knobs, touch panel, etc.

The processor 1010 (FIG. 10) may also process the detected signals regarding the shields 104A/104B to generate a control signal to control the PAPR 904 to change the air flow to the head protection device 100.

Accordingly, it can be seen that the head protection device 900 and the PAPR 904 may each have control circuitry. However, the control circuitry 910 in the head protection device 900 may be different than the control circuitry 920 in the PAPR. Additionally, the power source 930 may provide power for the PAPR 904, and may also provide power for the head protection device 900. Similarly, the power source 914 may provide power for the head protection device 900, and may also provide power for the PAPR 904.

Figure 10:
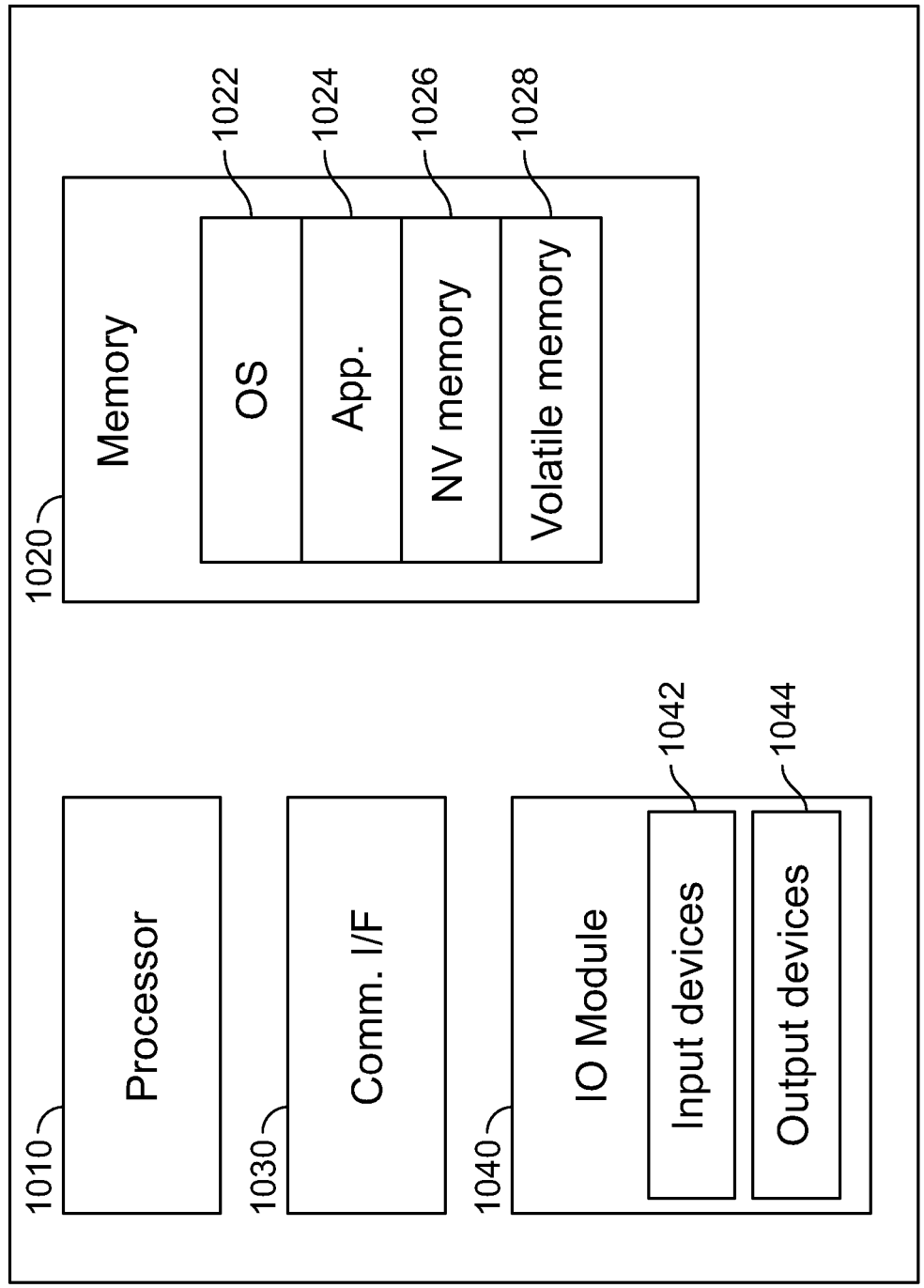
FIG. 10 shows a block diagram of an example control circuitry in accordance with aspects of the disclosure.

FIG. 10 shows a block diagram of an example control circuitry in accordance with an embodiment of the disclosure. Referring to FIG. 10, there is shown an example control circuitry 1000 that may be used with various embodiments of the disclosure. The control circuitry 1000 may comprise, for example, a processor 1010, memory 1020, a communication interface 1030, and an IO interface 1040. The processor 1010 may comprise, for example, multiple processors.

The memory 1020 may include non-volatile memory 1026 and volatile memory 1028. The storage described for holding local data may be part of the memory 1020 or comprise separate memory. The operating system 1022 and applications 1024 may be stored in, for example, the non-volatile memory 1026, and may be copied to volatile memory 1028 for execution. Various embodiments of the disclosure may use different memory architectures that are design and/or implementation dependent.

The communication interface 1030 may allow the control circuitry 1000 to communicate with other devices via, for example, a wired protocol such as USB, Ethernet, Firewire, etc., or a wireless protocol such as Bluetooth, Near Field Communication (NFC), Wi-Fi, etc. The wired or wireless protocol may also be, for example, a proprietary protocol. The various types of radios for communication may be referred to as a transceiver for the sake of simplicity. The communication may be, for example, with various sensors and/or devices that can relay sensor data. The communication interface 1030 may also be used to communicate with other networks such as local networks, cellular networks, etc.

The control circuitry 1000 may also comprise the IO module 1040 for communication with a user via the input devices 1042 and output information to be displayed on output devices 1044. The input devices 1042 may comprise, for example, switches, buttons, touch sensitive screen, which may be a part of a display, a microphone, etc. The input devices 1042 may also comprise, for example, various sensors, cameras, etc. The output devices 1044 may comprise, for example, the display, a speaker, LEDs, etc.

Accordingly, any one of numerous sensors such as switches, buttons, motion detectors, cameras, etc. may detect when a shield 104A or 104B is raised or lowered. The information that a shield 104A or 104B is raised or lowered may be processed by, for example, the processor 1010 and sent to an appropriate device such as, for example, the PAPR 904 via a wired or wireless communication using the communication interface 1030 in the control circuitry 1000 (or 910).

The processor 1010 may operate using different architectures in different embodiments. For example, the processor 1010 may use the memory 1020 to store instructions to execute, or the processor 1010 may have its own memory (not shown) for its instructions.

Various embodiments may use other architectures where the different functionalities may be grouped differently. For example, the grouping may be in different integrated circuit chips. Or the grouping may combine different devices such as the IO module 1040 and the communication interface 1030 together, etc.

Accordingly, it can be seen that the hard hat adapter 304 (or 700) may be used as a stand-alone device to which various attachments can be removably coupled, or as a part of a manufactured head protection device. The hard hat adapter 304 can clip into the slots of a hard hat and hold the welding helmet shell components in place. The hard hat adapter 304 may also be designed to removably couple to other hard hats that do not have slots. For example, the hard hat adapter 304 may be bolted to hard hat 302, or mounted to the hard hat 302 using a halo adapter, etc.

An embodiment of the hard hat adapter 304 has a pivot point for the outer face shield 104A that is not the same pivot point as for the inner face shield 104B. This allows the inner face shield 104B to clear the top of the hard hat 302 when it is raised. However, other embodiments may have the same pivot point for the outer face shield 104A and the inner face shield 104B depending on the hard hat 302. An embodiment of the hard hat adapter 304 places the pivot point for the inner face shield 104B below the brim of the hard hat 302 vertically and behind the center point horizontally (see FIG. 5). This pivot location makes the center of gravity low when the outer face shield 104A and the inner face shield 104B are raised.

A user may raise the outer face shield 104A and the inner face shield 104B to have access to their face while keeping the head seal and blower manifold in place. The pivot points of hard hat adapter 304 may allow the welding helmet to sit close to a user's face.

Accordingly, it can be seen that the disclosure provides for an example head protection device for a user that comprises a hard hat, a hard hat adapter coupled to the hard hat, and a helmet shell comprising an outer face shield and an inner face shield coupled to the hard hat adapter at a first pivot point, and a blower shell coupled to the hard hat adapter, wherein at least a portion of the blower shell is vertically below the outer face shield and the inner face shield.

The outer face shield is configured to rotate about the first pivot point and the inner face shield is configured to rotate about a second pivot point. When the outer face shield and the inner face shield are lowered, the outer face shield is configured to be raised without raising the inner face shield. When the outer face shield and the inner face shield are lowered, the outer face shield and the inner face shield are configured to be raised together. When the outer face shield and the inner face shield are raised, the inner face shield is configured to be lowered to cover a face of the user without lowering the outer face shield to cover the user's face. When the outer face shield and the inner face shield are raised, the inner face shield and the outer face shield are configured to be lowered together.

Furthermore, the blower shell is coupled to the hard hat adapter via a lower arm of the hard hat adapter, and the blower shell does not rotate when one or both of the outer face shield and the inner face shield are rotated. The blower shell may comprise at least one air conduit to receive powered air flow from outside the head protection unit. The head protection device may also comprise a light source that can be turned on or off.

Also, while the example head protection device includes a hard hat, various examples of the disclosure may be thought of as a face protection device that does not include a hard hat. In place of the hard hat, there may be a structure such as, for example, webbing, that may be used. This may be used, for example, for protecting the face when head protection is not needed. This may allow, for example, the face protection device to be lighter in weight and lower in cost.

The disclosure may also provide for an example hard hat adapter that comprises a coupling mechanism to removably couple the hard hat adapter to a hard hat, an upper arm configured to removably couple to an outer face shield and an inner face shield, and a lower arm configured to removably couple to a blower shell. The outer face shield and the inner face shield may be configured to removably couple to the hard hat adapter at a first pivot point of the hard hat adapter, where the first pivot point is on an upper arm of the hard hat adapter.

The outer face shield and the inner face shield are coupled to the hard hat adapter, and the outer face shield is configured to rotate about the first pivot point and the inner face shield is configured to rotate about a second pivot point that is below the first pivot point and behind the first pivot point. When the outer face shield and the inner face shield are lowered, the outer face shield is configured to be raised without raising the inner face shield. When the outer face shield and the inner face shield are lowered, the outer face shield and the inner face shield are configured to be raised together. When the outer face shield and the inner face shield are raised, the inner face shield is configured to be lowered to cover a face of a user without lowering the outer face shield to cover the user's face. When the outer face shield and the inner face shield are raised, the inner face shield and the outer face shield are configured to be lowered together.

The blower shell may be coupled to the hard hat adapter, and the blower shell does not rotate when one or both of the outer face shield and the inner face shield are rotated. A light source may be removably coupled to the blower shell, and the light source may be configured to turn on when the outer face shield is in a raised position, and turn off when the outer face shield is in a lowered position.

The hardhat adapter may also comprise an air conduit in the blower shell configured to receive air from a powered air purifying respirator (PAPR), where the PAPR is configured to deliver air at different air flow speeds when only the inner face shield is in a lowered position versus when both the inner face shield and the outer face shield are in the lowered position. That is, when only the inner face shield is lowered, the PAPR may deliver air at a first air flow speed, and when the inner face shield and the outer face shield are lowered, the PAPR may deliver air at a second air flow speed.

The various example descriptions provided for FIG. 9 may also be applied to other examples of the disclosure. Generally, any aspect of an example of the disclosure may apply to any other example of the disclosure as appropriate.

At least some of the present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise one or more application specific integrated circuit or chip. Some implementations may comprise a non-transitory machine-readable (e.g., computer readable) medium (e.g., FLASH memory, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g." and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What are claimed:

1. A hard hat adapter, comprising:
    a coupling mechanism configured to removably couple the hard hat adapter to a hard hat;
    an upper arm configured to removably couple to an outer face shield and an inner face shield;
    a lower arm configured to removably couple to a blower shell;
    a first pivot point at a first point on the upper arm and spaced from a second pivot point on the upper arm;
    wherein the outer face shield attaches to the upper arm at the first pivot point, and the inner face shield attaches to the upper arm at the second pivot point.

2. The hard hat adapter of claim 1, wherein the outer face shield is configured to rotate about the first pivot point and the inner face shield is configured to rotate about the second pivot point, wherein the second pivot point is below the first pivot point and behind the first pivot point with respect to a direction a user of the hard hat is facing.

3. The hard hat adapter of claim 2, wherein, when the outer face shield and the inner face shield are lowered, the outer face shield is configured to be raised without raising the inner face shield.

4. The hard hat adapter of claim 2, wherein, when the outer face shield and the inner face shield are lowered, the outer face shield and the inner face shield are configured to be raised together.

5. The hard hat adapter of claim 2, wherein, when the outer face shield and the inner face shield are raised, the inner face shield is configured to be lowered to cover a face of a user without lowering the outer face shield to cover the user's face.

6. The hard hat adapter of claim 2, wherein, when the outer face shield and the inner face shield are raised, the inner face shield and the outer face shield are configured to be lowered together.

7. The hard hat adapter of claim 2, wherein the blower shell is coupled to the hard hat adapter, and the blower shell does not rotate when one or both of the outer face shield and the inner face shield are rotated.

8. The hard hat adapter of claim 7, comprising a light source removably coupled to the blower shell wherein the light source is configured to:
    turn on when the outer face shield is in a raised position; and
    turn off when the outer face shield is in a lowered position.

9. The hardhat adapter of claim 1, further comprising an air conduit in the blower shell, the air conduit configured to receive air from a powered air purifying respirator (PAPR), wherein the PAPR is configured to deliver air at different air flow speeds when only the inner face shield is in a lowered position versus when both the inner face shield and the outer face shield are in the lowered position.

\* \* \* \* \*